(12) United States Patent
Renzi

(10) Patent No.: US 6,926,313 B1
(45) Date of Patent: Aug. 9, 2005

(54) HIGH PRESSURE CAPILLARY CONNECTOR

(75) Inventor: Ronald F. Renzi, Tracy, CA (US)

(73) Assignee: Sandia National Laboratories, Livermore, CA (US)

( * ) Notice: Subject to any disclaimer, the term of this patent is extended or adjusted under 35 U.S.C. 154(b) by 0 days.

(21) Appl. No.: 10/405,204

(22) Filed: Apr. 2, 2003

(51) Int. Cl.[7] .............................................. F16L 17/02
(52) U.S. Cl. ..................... 285/353; 285/342; 285/282.7
(58) Field of Search .......................... 285/382.7, 342, 285/343, 353

(56) References Cited

U.S. PATENT DOCUMENTS

| | | | |
|---|---|---|---|
| 3,677,577 A | | 7/1972 | Krauer et al. ................ 285/137 |
| 4,062,572 A | * | 12/1977 | Davis ........................... 285/55 |
| 4,083,702 A | * | 4/1978 | Hartigan et al. ............... 96/106 |
| 4,089,549 A | | 5/1978 | Vyse et al. ................... 285/137 |
| 4,313,828 A | * | 2/1982 | Brownlee ................ 210/198.2 |
| 4,529,230 A | * | 7/1985 | Fatula, Jr. .................... 285/341 |
| 4,619,473 A | * | 10/1986 | Someya ....................... 285/353 |
| 4,690,437 A | * | 9/1987 | Anderson, Jr. .............. 285/356 |
| 4,787,656 A | * | 11/1988 | Ryder .................... 285/148.23 |
| 4,915,419 A | | 4/1990 | Smith, III .................... 285/26 |
| 4,991,883 A | * | 2/1991 | Worden ................... 285/334.4 |
| 4,995,646 A | | 2/1991 | Johnston et al. ............ 285/137 |
| 5,209,525 A | | 5/1993 | Ito .............................. 285/137 |
| 5,234,235 A | * | 8/1993 | Worden ................... 285/334.4 |
| 5,288,113 A | * | 2/1994 | Silvis et al. ................. 285/342 |
| 5,366,620 A | | 11/1994 | Schick |
| 5,419,208 A | | 5/1995 | Schick |
| 5,472,598 A | | 12/1995 | Schick |
| 5,482,628 A | | 1/1996 | Schick |
| 5,487,569 A | | 1/1996 | Silvis et al. |
| 5,494,641 A | | 2/1996 | Krstanovic |
| 5,534,152 A | | 7/1996 | Schick |
| 5,540,464 A | | 7/1996 | Picha |
| 5,644,395 A | | 7/1997 | Folta |

(Continued)

OTHER PUBLICATIONS

U.S. Appl. No. 10/350,541, filed Jan. 24, 2003, Renzi.
U.S. Appl. No. 10/350,628, filed Jan. 24, 2003, Renzi.
U.S. Appl. No. 10/351,714, filed Jan. 27, 2003, Renzi.
U.S. Appl. No. 10/405,842, filed Apr. 2, 2003, Renzi et al.
U.S. Appl. No. 10/350,626, filed Jan. 24, 2003, Renzi.

Primary Examiner—Eric K. Nicholson
(74) Attorney, Agent, or Firm—Fliesler Meyer LLP

(57) ABSTRACT

A high pressure connector capable of operating at pressures of 40,000 psi or higher is provided. This connector can be employed to position a first fluid-bearing conduit that has a proximal end and a distal end to a second fluid-bearing conduit thereby providing fluid communication between the first and second fluid-bearing conduits. The connector includes (a) an internal fitting assembly having a body cavity with (i) a lower segment that defines a lower segment aperture and (ii) an interiorly threaded upper segment, (b) a first member having a first member aperture that traverses its length wherein the first member aperture is configured to accommodate the first fluid-bearing conduit and wherein the first member is positioned in the lower segment of the internal fitting assembly, and (c) a second member having a second member aperture that traverses its length wherein the second member is positioned in the upper segment of the fitting assembly and wherein a lower surface of the second member is in contact with an upper surface of the first member to assert a compressive force onto the first member and wherein the first member aperture and the second member aperture are coaxial.

33 Claims, 4 Drawing Sheets

U.S. PATENT DOCUMENTS

| | | | |
|---|---|---|---|
| 5,736,036 A | 4/1998 | Upchurch et al. | |
| 5,846,396 A | 12/1998 | Zanzucchi et al. | |
| 5,855,229 A | 1/1999 | Gluf, Jr. | 137/884 |
| 5,865,474 A | 2/1999 | Takahashi | 285/124.1 |
| 5,987,735 A | 11/1999 | Horning et al. | |
| 5,988,703 A | 11/1999 | Craig | 285/288.1 |
| 6,083,763 A | 7/2000 | Balch | |
| 6,086,825 A | 7/2000 | Sundberg et al. | |
| 6,090,251 A | 7/2000 | Sundberg et al. | |
| 6,102,449 A | 8/2000 | Welsh | |
| 6,102,897 A | 8/2000 | Lang | |
| 6,129,331 A | 10/2000 | Henning et al. | |
| 6,190,616 B1 | 2/2001 | Jovanovich et al. | |
| 6,209,928 B1 * | 4/2001 | Benett et al. | 285/124.1 |
| 6,224,728 B1 | 5/2001 | Oborny et al. | |
| 6,267,143 B1 | 7/2001 | Schick | |
| 6,273,478 B1 * | 8/2001 | Benett et al. | 285/346 |
| 6,293,725 B1 | 9/2001 | Winkvist | |
| 6,312,960 B1 | 11/2001 | Balch et al. | |
| 6,319,476 B1 | 11/2001 | Victor, Jr. et al. | |
| 6,344,145 B1 | 2/2002 | Garguilo et al. | |
| 6,358,387 B1 | 3/2002 | Kopf-Sill et al. | |
| 6,488,318 B1 * | 12/2002 | Shim | 285/322 |
| 2001/0045235 A1 | 11/2001 | Schick | |

* cited by examiner

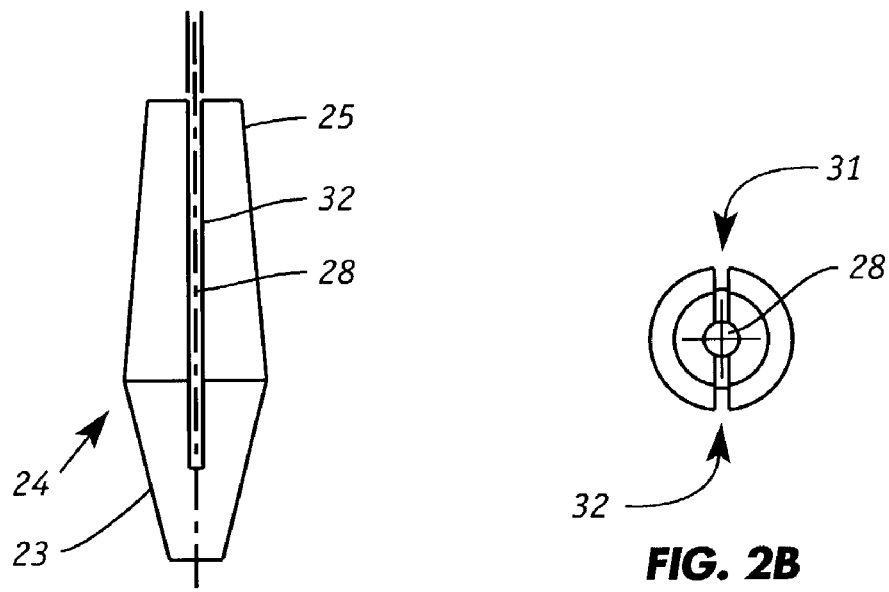
FIG. 2A
FIG. 2B
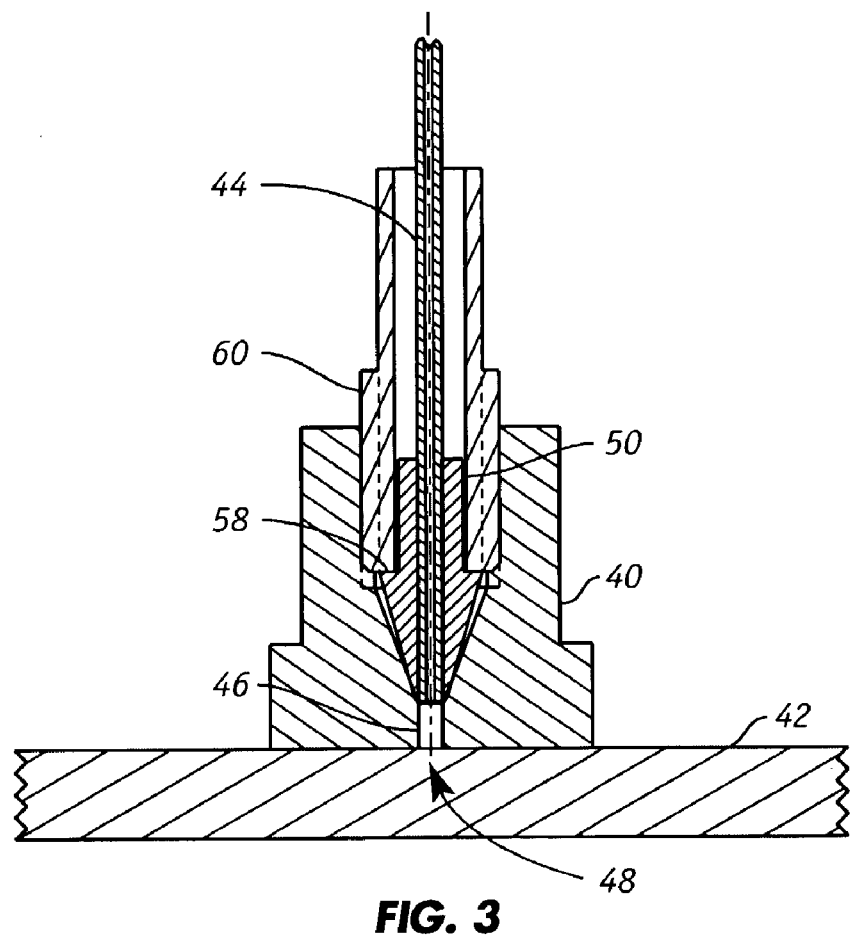
FIG. 3

HIGH PRESSURE CAPILLARY CONNECTOR

This invention was made with Government support under Contract No. DE-AC04-94AL85000 awarded by the U.S. Department of Energy to Sandia Corporation. The Government has certain rights to the invention.

FIELD OF THE INVENTION

The present invention relates generally to microfluidic systems and more particularly to structures which facilitate the introduction of fluids into devices having microfluidic channels.

BACKGROUND OF THE INVENTION

Devices for performing chemical analysis have in recent years become miniaturized. For example, microfluidic devices have been constructed using microelectronic fabrication and micromachining techniques on planar substrates such as glass or silicon which incorporate a series of interconnected channels or conduits to perform a variety of chemical analysis such as capillary electrophoresis (CE) and high-performance liquid chromatography (HPLC).

Microfluidic substrates have networks of chambers connected by channels which have mesoscale dimensions, where at least one dimension is usually between 0.1 microns and 500 microns. Such microfluidic substrates may be fabricated using photolithographic techniques similar to those used in the semi-conductor industry, and the resulting devices can be used to perform a variety of sophisticated chemical and biological analytical techniques. Microfluidic analytical technology has a number of advantages, including the ability to use very small sample sizes, typically on the order of nanoliters. The substrates may be produced at a relatively low cost, and can be formatted to perform numerous specific analytical operations, including mixing, dispensing, valving, reactions, and detections.

Another recently developed class of sample-receiving microfluidic substrates includes substrates having a capillary interface that allows compounds to be brought onto the test substrate from an external source, and which can be advantageously used in a number of assay formats for high-throughput screening applications. These assay formats include fluorogenic assays, fluorescence polarization assays, non-fluorogenic mobility shift assays, dose response assays, and calcium flux cell-based assays.

Other applications for microfluidic devices include diagnostics involving biomolecules and other analytical techniques such as micro total analysis systems. Such devices, often referred to in the art as "microchips," also may be fabricated from plastic, with the channels being etched, machined or injection molded into individual substrates. Multiple substrates may be suitably arranged and laminated to construct a microchip of desired function and geometry. In all cases, the channels used to carry out the analyses typically are of capillary scale dimension.

To fully exploit the technological advances offered by the use of microfluidic devices and to maintain the degree of sensitivity for analytical techniques when processing small volumes, e.g., microliters or less, connectors which introduce and/or withdraw fluids, i.e., liquids and gases, from the device, as well as interconnect microfluidic devices, are a crucial component in the use and performance of the microfluidic device.

A common technique used in the past involves bonding a length of tubing to a port on the microfluidic device with epoxy or other suitable adhesive. Adhesive bonding is unsuitable for many chemical analysis applications because the solvents used attack the adhesive which can lead to channel clogging, detachment of the tubing, and/or contamination of the sample and/or reagents in or delivered to the device. Furthermore, adhesive bonding results in a permanent attachment of the tubing to the microfluidic device which makes it difficult to change components, i.e., either the microfluidic device or the tubing, if necessary. Thus assembly, repair and maintenance of such devices become labor and time intensive, a particularly undesirable feature when the microfluidic device is used for high throughput screening of samples such as in drug discovery.

To avoid problems associated with adhesive bonding, other techniques have been proposed in the past, e.g., press fitting the tubing into a port on the microfluidic device. However, such a connection typically is unsuitable for high-pressure applications such as HPLC. Additionally, pressing the tubing into a port creates high stress loads on the microfluidic device which could lead to fractures of the channels and/or device.

Other methods involved introducing liquids into an open port on the microfluidic device with the use of an external delivery system such as a pipette, but this technique also is undesirable due to the possibility of leaks and spills which may lead to contamination. In addition, the fluid is delivered discretely rather than continuously. Moreover, the use of open pipetting techniques does not permit the use of elevated pressure for fluid delivery such as delivered by a pump, thereby further restricting the applicability of the microfluidic device.

Therefore, a need exists for an improved microfluidic connector which is useful with all types of microfluidic devices and provides an effective, high pressure, low fluid dead volume seal. The connector also should overcome the disadvantages and limitations described above, including chemical compatibility problems resulting from the use of adhesive bonding techniques.

SUMMARY OF THE INVENTION

The present invention is based in part on the development of a high pressure connector capable of operating at pressures of 40,000 psi and higher.

In one aspect, the invention is directed to a connector for positioning a lower segment fluid-bearing conduit that has a proximal end and a distal end to a second fluid-bearing conduit thereby providing fluid communication between the first and second fluid-bearing conduits that includes:

an internal fitting assembly having a body cavity with (i) a lower segment that defines a first aperture and (ii) an interiorly threaded upper segment;

a first member having a first member aperture that traverses its length wherein the first member aperture is configured to accommodate the first fluid-bearing conduit and wherein the first member is positioned in the lower segment of the internal fitting assembly; and a second member having a second member aperture that traverses its length wherein the second member is positioned in the upper segment of the fitting assembly and wherein a lower surface of the second member is in contact with an upper surface of the first member to assert a compressive force onto the first member and wherein the first member aperture and the second member aperture are coaxial.

In a preferred embodiment of the connector, (a) the lower segment has a body cavity that has an interior frustoconical shape, (b) the first member comprises a collet that has a tapered, lower outer portion and which defines a collet aperture that extends from a proximal end to the distal end of the collet with the distal end being in communication with the lower segment aperture of the internal fitting assembly, wherein the collet aperture is defined by an inner wall having one or more slots, and (c) the second member comprises a fastener defining an internal cavity into which the collet is secured wherein the fastener has an upper portion with a fastener aperture that is coaxial with the collet aperture at the proximal end of the collet, wherein the first fluid-bearing conduit can be positioned within the lower segment, collet, and fastener apertures and wherein upon treading the fastener into the internal fitting assembly causes the slots to compress thereby reducing the size of the collet aperture and increasing the force applied to a first fluid-bearing conduit.

In another embodiment of the connector, (a) the lower segment has a body cavity that has an interior frustoconical shape, (b) the first member comprises a ferrule that has a tapered, lower outer portion and which defines a ferrule aperture that extends from a proximal end to the distal end with the distal end being in communication with the lower segment aperture of the internal fitting assembly, and (c) the second member comprises a fastener defining an internal cavity into which the ferrule is secured wherein the fastener has an upper portion with a fastener aperture that is coaxial with the ferrule aperture at the proximal end of the ferrule, wherein the first fluid-bearing conduit is positioned within the lower segment collet, and fastener and wherein upon threading the fastener into the internal fitting assembly causes compressive force onto the ferrule and increasing the force applied to a first fluid-bearing conduit.

BRIEF DESCRIPTION OF THE DRAWINGS

FIGS. 2A and 2B are the side elevational and top cross sectional views, respectively, of a collet or ferrule;

FIG. 3 is a cross sectional view of a second high pressure capillary connector;

DESCRIPTION OF THE PREFERRED EMBODIMENTS

The capillary connectors of the present invention will be described to connect capillaries to a microscale device, however, it is understood that the use of these connectors is not so limited. The connectors, for example, can be employed as port features in a valve body. In addition, they can be employed for capillary to capillary connections with elbows, tees, crosses, and other channel geometries as further discussed herein.

Figure 1A:
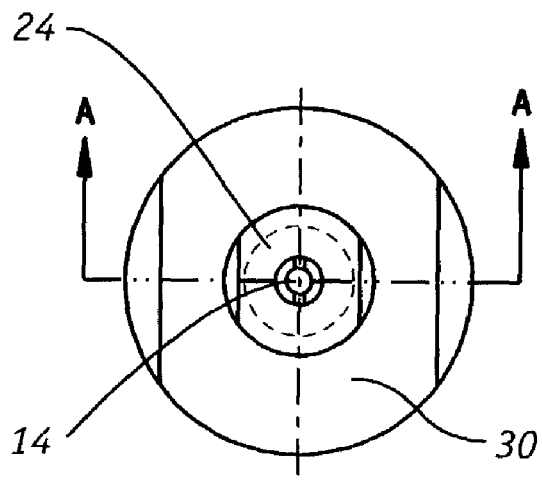
FIG. 1A is the top plan view of the high pressure capillary connector and FIG. 1B is a cross sectional view along the A—A line of FIG. 1A (shown connected to a substrate)
Figure 1B:
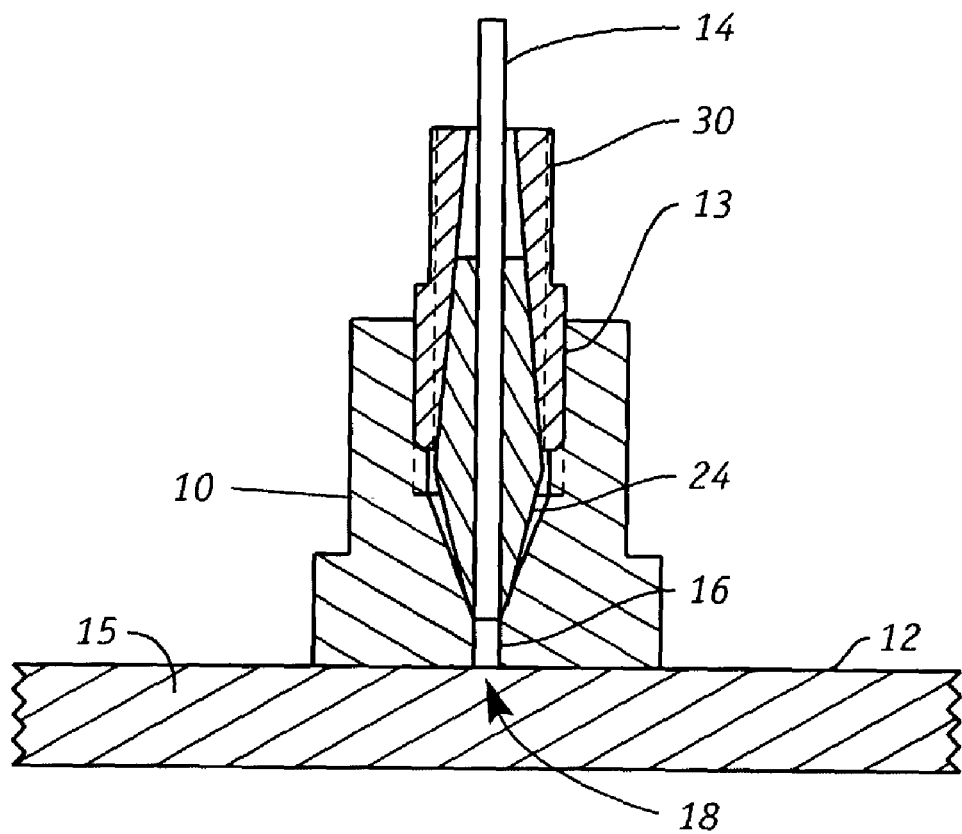

Referring to FIGS. 1A and 1B, the high pressure capillary connector includes a manifold 10 that is attached to the external surface 12 of a substrate 15, e.g., microscale device, and which has an inlet or outlet port 18 facing external surface 12. The manifold 10 is preferably made of any suitable stiff material that can be bonded, e.g., with epoxy, to external surface 12. Preferred materials include, for example, metal such as stainless steel and ceramics. Alternatively, the compression manifold can be attached to external surface 12 by mechanical means such as clamps or screws. In another embodiment, the manifold and the external surface are formed as an integral unit.

The interior surface of manifold 10 has a lower internal surface defining a conical cavity having a lower bore 16 whose length is parallel to the major axis of the compression manifold. The conical cavity is configured to receive collet or ferrule 24 into which a capillary 14 is inserted and which is secured to manifold 10 by threaded annular fastener 30. The interior surface of manifold 10 also has an upper internal surface 13 that has a cylindrical cross section and that is threaded to mate with the threaded annular fastener 30.

As shown in FIG. 1B, capillary 14 fits inside internal bore 16 and comes in direct contact with the internal bore surface. No mating sleeve that is positioned around the outer surface of tube 14 is needed.

As shown in FIGS. 2A and 2B, the collet or ferrule 24 has an elongated structure with an aperture 28 traversing its length. The diameter of aperture 28 is slightly larger than the outer diameter of a capillary that is to be positioned therein. The external surface of elongate structure of collet 24 is preferably tapered at both ends 23, 25; in addition, slits or notches 31, 32 are formed on opposite sides of the wall of the collet 26. Although two slits are preferred, any number of slits typically ranging from 1–4 can be employed. The slits 31, 32 terminate near the bottom of the collet 24 which is preferably made of a suitable material that deforms with mechanical compression. Preferred materials include, for example, polymers such as polyether ether ketone (PEEK). The external surface of the lower portion 23 of collet 24 matches at least a portion of the internal contour of compression manifold 10. Similarly, the external surface of the upper portion 25 of collet 24 matches at least a portion of the internal contour of annular threaded fastener 30.

In practice, connecting a capillary to a microscale device entails first configuring an assembly comprising collet 24 and annular threaded fastener 30 that is disposed on the upper portion of collet 24. Thereafter, annular threaded fastener 30, with the collet attached, is screwed into manifold 10 which has been attached to the surface of microscale device so that port 18 (FIG. 1B) of the manifold 10 is aligned to a channel opening on the surface of the microscale device. As the annular threaded fastener is tightened into the manifold, the compressive force causes the collet 24 to deform at the slits 31, 32 so that the wall of aperture 28 collapses onto and grip the capillary. In addition, the force also causes the exterior tapered end 23 of the collet to deform against the internal surface of the manifold thereby creating a fluid-tight seal.

While the collet and annular threaded fastener have been described as two separate components, they can also be manufactured as an integral unit. Thus, the threaded annular fastener can be made of the same material as the collet. With the inventive capillary connector, the collet prevents the capillary from being extruded from the manifold even at high operating pressures. Conversely, removing the capillary from the collet simply requires unthreading or unscrewing the threaded fastener.

Figure 4A:
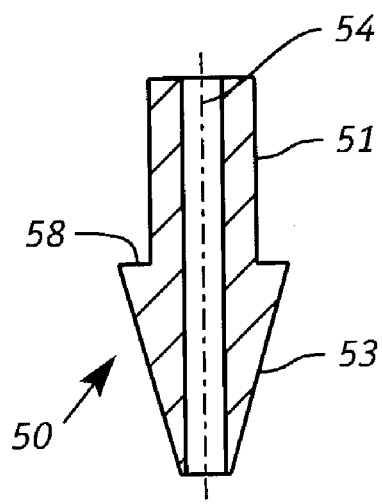
FIGS. 4A and 4B are cross sectional and perspective views, respectively, of a ferrule.
Figure 4B:
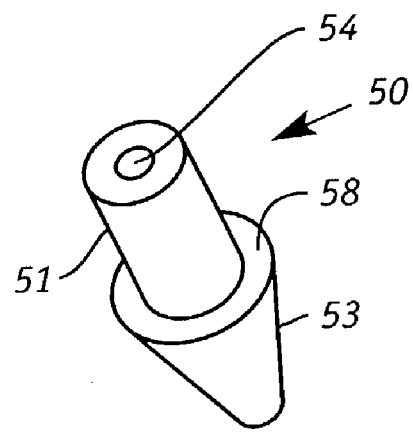

FIG. 3 illustrates a second embodiment of a capillary connector that includes a manifold 40 that is attached to the external surface 42 of a microscale device and which has an inlet or outlet port 48 facing the external surface 42. Manifold 40 can be of the same design as manifold 10 (as shown in FIGS. 1A and 1B), thus it has an interior surface that defines a conical cavity having a lower bore 46 whose length is parallel to the major axis of the manifold 40. The interior surface of manifold 40 also defines an upper internal surface that has a cylindrical cross section and that is threaded to mate with threaded annular fastener 60. The conical cavity configured to receive a ferrule 50 which fits into the conical cavity of the manifold. Ferrule 50 is preferably made of a material that deforms when pressure is applied, and that adheres well to epoxy such as a thermoplastic polyetherimide polymer that is available as ULTEM from General Electric, to ensure good capillary to ferrule adhesion. As further shown in FIGS. 4A and 4B, ferrule 50 has a cylindrical upper or proximal portion 51, a tapered distal portion 53 with a protruding ridge or shoulder 58 around the circumference where the tapered distal portion begins. Ferrule 50 has an internal aperture 54 that runs the length of the ferrule to support a capillary tube. The upper surface of shoulder 58 of ferrule 50 is disposed on the end of threaded fastener 60. Capillary tube 44 is inserted into aperture 54 of ferrule 50. Capillary 44 is bonded to ferrule 50 using, for example, a two part epoxy.

To connect a capillary tube using the connector, an assembly comprising ferrule 50 and threaded fastener 60 is first configured. A capillary is inserted into internal aperture 54 of ferrule 50 and thereafter the screwing of the annular threaded fastener 60 into compression manifold 40 compresses the tapered end of ferrule 50 against the conical cavity in the compression manifold to form a fluid-tight seal. While the ferrule and annular threaded fastener have been described as two separate components, they can also be manufactured as an integral unit. Thus, the annular threaded fastener can be made of the same material as the ferrule.

Ferrule 50 is preferably made of, or at least is coated with, a material that bonds to the capillary tube. For example, since capillary tubes typically have a polyimide sheating on their exterior surfaces, fabricating the collet with polyether imide will insure that the two surfaces will form chemical bonds to insure a good fit and to prevent the capillary from extruding when operating at high pressures. Alternatively, adhesives can be used to bond the capillary and the collet. Since ferrule 50 and manifold 40 form a tight seal, no adhesive will contaminate the fluid being transported by capillary 44.

Figure 5:
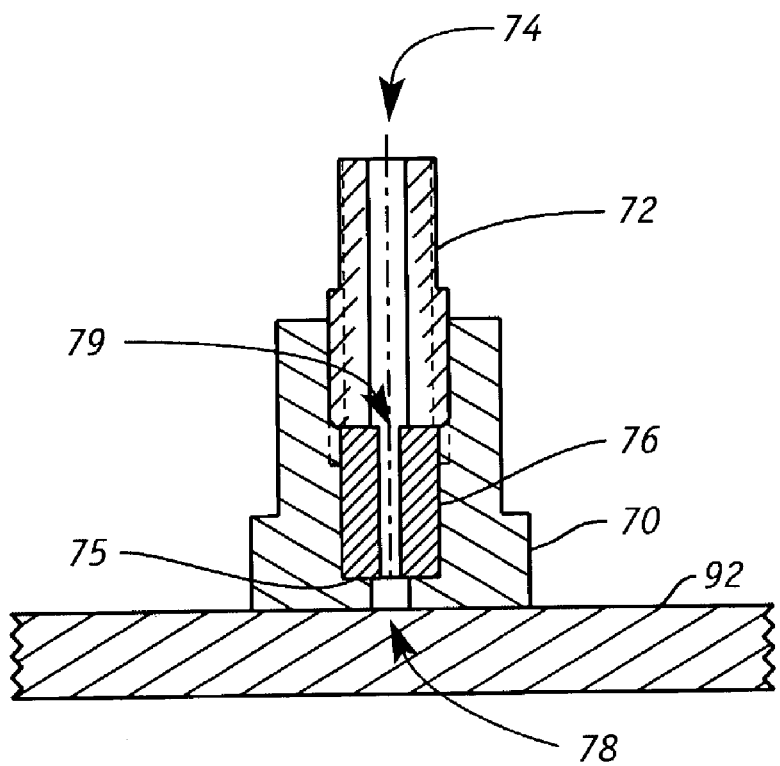
FIG. 5 is a cross view of a third high pressure connector.

FIG. 5 illustrates another embodiment of a capillary connector that includes a manifold 70 that is attached to the external surface 92 of a microscale device and which has an inlet or outlet port 78 facing the external surface 92. The manifold 70 has a threaded upper interior surface that defines a cavity dimensioned to accommodate threaded lug 72. The manifold 70 has a lower cavity dimensioned to accommodate ferrule 76. The lug 72 is preferably made of metal and has an aperture 74 whereas ferrule 76 is preferably made of a deformable material such as, for example, rubber and has an aperture 79. The apertures 74 and 79 are coaxial to the major axis of the compression manifold 70 and the diameter of aperture is preferably larger than that of aperture 79. The lower portion of manifold 70 defines a shoulder 75 onto which ferrule 76 is positioned.

In use, a capillary is first inserted into aperture 79 of ferrule 76 which is then inserted into the manifold 70 with the distal end of the capillary positioned adjacent to port 78 of the manifold 70. Next the metal lug 72 is threaded into the manifold thereby compressing the elastomeric material of the ferrule and gripping the outer surface of the capillary.

The high pressure connectors of the present invention are particularly suited for connecting capillary tubes to the microchannels, i.e., fluid-bearing conduits, of a microscale analytic device. Preferred capillaries have circular inner diameters that range from about 1 micron to 250 microns and outer diameters that range from about 5 microns to 500 microns. Capillaries are available commercially from numerous sources including, for example, Polymicro Technologies LLC (Phoenix, Ariz.). The inventive fittings are capable of withstanding pressures of up to at least about 40,000 psi. There are numerous analysis operations, such as high pressure liquid chromatography, that are desirably carried out on microscale devices and that require the application of high pressure. These microscale devices have microfluidic channels, e.g., sealed enclosed groove, depression, tube, capillary, which is adapted to handle small volumes of fluid. Typically, the channel is a tube, channel or conduit having at least one subsection with at least one cross-sectional dimension of between about 0.1 microns and 500 microns, and typically less than 100 microns. Microscale devices or substrates refer to any microfluidic member that has an integrated network of microfluidic channels disposed therein. The particular design or configuration of the internal structure of the substrate is not critical. Such devices are also referred as microfluidic or microscale wafers or chips.

The microscale devices include microfluidic channels, e.g., sealed enclosed groove, depression, and tube, which is adapted to handle small volumes of fluid. The microscale device or substrate is preferably fabricated from glass, quartz, silicon or plastic by conventional techniques including LIGA (an acronym for the German for lithography, electroplating, and molding), deep x-ray lithography, silicon surface micromachining and lithography, electric discharge machining, and direct laser additive fabrication. In addition, commercially available microscale devices can be modified with appropriate dimensioned inlet and/or outlet ports. The microscale may include reaction cells, reservoirs, and other structures that are interconnected by a network of microchannels and a series of micropumps. Such microscale devices are further described, for example, in U.S. Pat. No. 5,846,396 to Zanzucchi, et al. which is incorporated herein.

Connectors of the present invention can also be employed to connect two capillaries together. This is accomplished by employing two connectors each supporting a capillary and attaching the lower surfaces of the two manifolds together so that the manifold aperture of one faces that of the other. In this fashion, the two capillaries are in fluid communication.

Figure 6A:
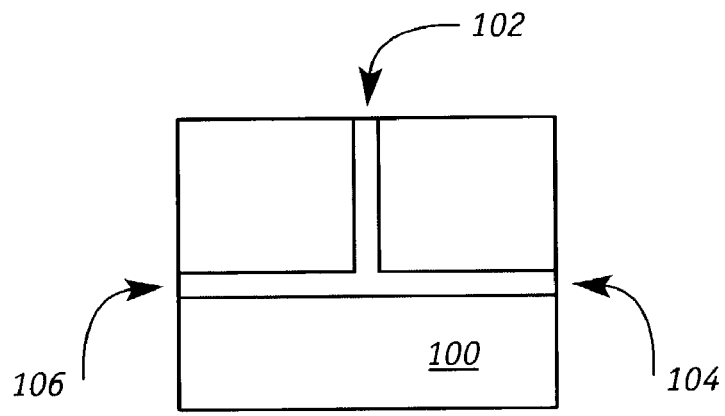
FIGS. 6A, 6B, and 6C are schematics of substrates for tee, elbow and cross connections.
Figure 6B:
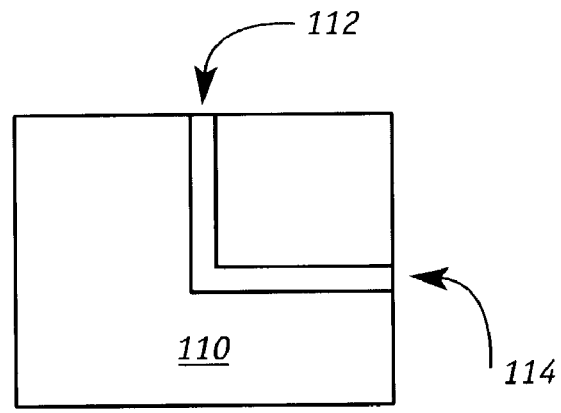
Figure 6C:
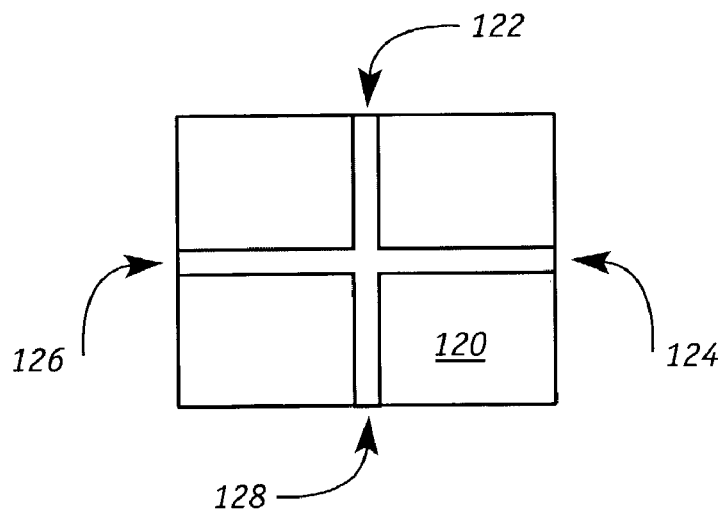

FIGS. 6A, 6B, and 6C illustrate substrates useful for connecting a capillary to one or more other capillaries by way of a tee, elbow, and cross connection configurations, respectively. As shown in FIG. 6A, substrate 100 has a tee-shaped channel having ports 102, 104, and 106. The capillary connector of the present invention can be employed to connect a capillary to each of the three ports and thereby provide fluid communication between them. FIG. 6B shows substrate 110 with two ports 112 and 114. The channel connecting the ports is elbow-shaped. Finally, FIG. 6C shows substrate 120 with four ports 122, 124, 126, and 128 that interconnect cross-shaped channels. Connectors of the present invention can connect a capillary to each port.

Although only preferred embodiments of the invention are specifically disclosed and described above, it will be appreciated that many modifications and variations of the present invention are possible in light of the above teachings and within the purview of the appended claims without departing from the spirit and intended scope of the invention.

What is claimed is:

1. A connector for connecting a fluid-bearing conduit to an inlet or outlet port of a device thereby providing fluid communication between the fluid-bearing conduit and the inlet or outlet port comprising:
   an internal fitting assembly having a body cavity with (i) a lower segment that has an interior frustoconical shaped surface and that defines a lower segment aperture that is in fluid communication with the inlet or outlet port and (ii) an interiorly threaded upper segment;
   a first member having a first member aperture that traverses its length wherein the first member aperture is configured to accommodate the fluid-bearing conduit wherein the first member has an upper surface and a frustoconical lower surface, and wherein the first member is positioned in the lower segment of the internal fitting assembly; and
   a second member having a second member aperture that traverses its length wherein the second member is engaged in the upper segment of the fitting assembly and wherein a lower surface of the second member is in contact with an upper surface of the first member to assert a compressive force onto the first member wherein the frustoconical lower surface of the first member forms a fluid-tight seal and, wherein the first member aperture and the second member aperture are coaxial and wherein the aperture of the first or second member is reduced and applies an increasing force to a first fluid-bearing conduit when compressively engaged by the second member, and wherein the combination of actions of the first member and the second member when engaged in the lower segment of the internal fitting assembly allow for fluid-tight seals to at least 40,000 psi without extrusion of the fluid-bearing conduit.

2. The connector of claim 1 wherein:
   the first member comprises a collet which defines a collet aperture that extends from a proximal end to the distal end of the collet with the distal end being in communication with the lower segment aperture of the internal fitting assembly, wherein the collet aperture is defined by an inner wall having one or more slits wherein the collet has a tapered upper surface and a frustoconical lower surface; and
   the second member comprises a fastener defining an internal cavity into which the collet is secured wherein the fastener has an upper portion with a fastener aperture that is coaxial with the collet aperture at the proximal end of the collet, wherein the fluid-bearing conduit can be positioned within the lower segment, collet, and fastener apertures and wherein upon threading the fastener into the internal fitting assembly causes the slits to compress thereby reducing the size of the collet aperture and increasing the force applied to a fluid-bearing conduit.

3. The connector of claim 1 wherein the internal fitting assembly is made of metal or ceramics.

4. The connector of claim 2 wherein the collet is made of a deformable material.

5. The connector of claim 2 wherein the fastener is made of a deformable material.

6. The connector of claim 2 wherein the collet and fastener comprise an integral structure.

7. The connector of claim 2 wherein the fluid-bearing conduit is a capillary having an internal diameter of 5 microns to 250 microns.

8. The connector of claim 1 wherein the first member is made of a deformable material.

9. The connector of claim 1 wherein the second member is made of metal.

10. The connector of claim 1 wherein at least a portion of the exterior surface of the second member is threaded.

11. The connector of claim 1 wherein the fluid-bearing conduit is a capillary having an internal diameter of 5 microns to 250 microns.

12. The connector of claim 1 wherein the diameter of the second member aperture is larger than the diameter of the first member aperture.

13. The connector of claim 1 wherein the frustoconical lower surface of the first member seals adjacent a distal end of the fluid-bearing conduit.

14. An apparatus that connects a first capillary to one or more other capillaries that comprises:
   (a) a device having a first port and at least one other port wherein the ports are connected by one or more channels within the device;
   (b) a first connector that is attached to the device that comprises:
      (i) a first internal fitting assembly having a body cavity with (i) a lower segment that has an interior frustoconical shaped surface and that defines a lower segment aperture that is in fluid communication with the first port and (ii) an interiorly threaded upper segment;
      (ii) a first member having a first member aperture that traverses its length wherein the first member aperture is configured to accommodate the first capillary wherein the first member has an upper surface and a frustoconical lower surface and wherein the first member is positioned in the lower segment of the internal fitting assembly; and
      (iii) a second member having a second member aperture that traverses its length wherein the second member is engaged in the upper segment of the first fitting assembly and wherein a lower surface of the second member is in contact with an upper surface of the first member to assert a compressive force onto the first member wherein the frustoconical lower surface of the first member forms a fluid-tight seal and, wherein the first member aperture and the second member aperture are coaxial and wherein the aperture of the first or second member is reduced and applies an increasing force to a first capillary when compressively engaged by the second member, and wherein the combination of actions of the first member and the second member when engaged in the lower segment of the internal fitting assembly allow for fluid-tight seals to at least 40,000 psi without extrusion of the first capillary; and
   (c) a second connector that is attached to the device that comprises:
      (i) a first internal fitting assembly having a body cavity with (i) a lower segment that has an interior frustoconical shaped surface and that defines a lower segment aperture that is in fluid communication with a second port and (ii) an interiorly threaded upper segment;
      (ii) a first member having a first member aperture that traverses its length wherein the first member aperture is configured to accommodate the second capillary wherein the first member has an upper surface and a frustoconical lower surface and wherein the first member is positioned in the lower segment of the internal fitting assembly; and (iii) a second member having a second member aperture that traverses its length wherein the second member is engaged in the upper segment of the first fitting assembly and wherein a lower surface of the second member is in contact with an upper surface of the first member to assert a compressive force onto the first member wherein the frustoconical lower surface of the first member forms a fluid-tight seal and, wherein the first member aperture and the second member aperture are coaxial and wherein the aperture of the first or second member is reduced and applies an increasing force to a second capillary when compressively engaged by the second member, and wherein the combination of actions of the first member and the second member when engaged in the lower segment of the internal fitting assembly allow for fluid-tight seals to at least 40,000 psi without extrusion of the second capillary.

15. The apparatus of claim 14 wherein the first port and the second port are connected by a channel that has an elbow configuration.

16. The apparatus of claim 14 further comprising (d) a third connector that is attached to the device that comprises:
    (i) a first internal fitting assembly having a body cavity with (i) a lower segment that has an interior frustoconical shaped surface and that defines a lower segment aperture that is in fluid communication with a third port and (ii) an interiorly threaded upper segment;
    (ii) a first member having a first member aperture that traverses its length wherein the first member aperture is configured to accommodate the third capillary wherein the first member has an upper surface and a tapered, lower surface and wherein the first member is positioned in the lower segment of the internal fitting assembly; and
    (iii) a second member having a second member aperture that traverses its length wherein the second member is engaged in the upper segment of the first fitting assembly and wherein a lower surface of the second member is in contact with an upper surface of the first member to assert a compressive force onto the first member wherein the frustoconical lower surface of the first member forms a fluid-tight seal and, wherein the first member aperture and the second member aperture are coaxial and wherein the aperture of the first or second member is reduced and applies an increasing force to a third capillary when compressively engaged by the second member, and wherein the combination of actions of the first member and the second member when engaged in the lower segment of the internal fitting assembly allow for fluid-tight seals to at least 40,000 psi without extrusion of the third capillary.

17. The apparatus of claim 16 wherein the first, second and third ports are connected by channels that define a tee configuration.

18. The apparatus of claim 16 further comprising (e) a fourth connector that is attached to the device that comprises:
    (i) a first internal fitting assembly having a body cavity with (i) a lower segment that has an interior frustoconical shaped surface and that defines a lower segment aperture that is in fluid communication with a fourth port and (ii) an interiorly threaded upper segment;
    (ii) a first member having a first member aperture that traverses its length wherein the first member aperture is configured to accommodate the fourth capillary wherein the first member has an upper surface and a frustoconical lower surface and wherein the first member is positioned in the lower segment of the internal fitting assembly; and
    (iii) a second member having a second member aperture that traverses its length wherein the second member is engaged in the upper segment of the first fitting assembly and wherein a lower surface of the second member is in contact with an upper surface of the first member to assert a compressive force onto the first member wherein the frustoconical lower surface of the first member forms a fluid-tight seal and, wherein the first member aperture and the second member aperture are coaxial and wherein the aperture of the first or second member is reduced and applies an increasing force to a fourth capillary when compressively engaged by the second member, and wherein the combination of actions of the first member and the second member when engaged in the lower segment of the internal fitting assembly allow for fluid-tight seals to at least 40,000 psi without extrusion of the fourth capillary.

19. The apparatus of claim 18 wherein, for each of the first, second, third and fourth connectors the internal fitting assembly is made of metal or ceramics.

20. The apparatus of claim 18 wherein, for each of the first, second, third, and fourth connectors, the first member is made of a deformable material.

21. The apparatus of claim 18 wherein, for each of the first, second, third, and fourth connectors, the second member is made of metal.

22. The apparatus of claim 18 wherein, for each of the first, second, third, and fourth connectors, at least a portion of the exterior surface of the second member is threaded.

23. The apparatus of claim 18 wherein, for each of the first, second, third, and fourth connectors, the capillary has an internal diameter of 5 microns to 250 microns.

24. The apparatus of claim 18 wherein, for each of the first, second, third, and fourth connectors, the diameter of the second member aperture is larger than the diameter of the first member aperture.

25. The apparatus of claim 18 wherein the first, second, third and fourth ports are connected by channels that define a cross configuration.

26. The apparatus of claim 18 wherein the device comprises a microscale device.

27. The apparatus of claim 18 wherein, for each of the connectors, the first member comprises a collet which defines a collet aperture that extends from a proximal end to the distal end of the collet with the distal end being in communication with the lower segment aperture of the internal fitting assembly, wherein the collet aperture is defined by an inner wall having one or more slits wherein the collet has a tapered, upper surface and a frustoconical lower surface; and the second member comprises a fastener defining an internal cavity into which the collet is secured wherein the fastener has an upper portion with a fastener aperture that is coaxial with the collet aperture at the proximal end of the collet, wherein the capillary can be positioned within the lower segment, collet, and fastener apertures and wherein upon threading the fastener into the internal fitting assembly causes the slits to compress thereby reducing the size of the collet aperture and increasing the force applied to a capillary.

28. The apparatus of claim 27 wherein, for each of the first, second, third, and fourth connectors, the internal fitting assembly is made of metal or ceramics.

29. The apparatus of claim 27 wherein, for each of the first, second, third, and fourth connectors, the collet is made of a deformable material.

30. The apparatus of claim 27 wherein, for each of the first, second, third, and fourth connectors, the fastener is made of a deformable material.

31. The apparatus of claim 27 wherein, for each of the first, second, third, and fourth connectors, the collet and fastener comprise an integral structure.

32. The apparatus of claim 27 wherein, for each of the first, second, third, and fourth connectors, the capillary having an internal diameter of 5 microns to 250 microns.

33. The apparatus of claim 27 wherein the device comprises a microscale device.

\* \* \* \* \*